(12) United States Patent
Kondo

(10) Patent No.: US 10,828,430 B2
(45) Date of Patent: Nov. 10, 2020

(54) MEDICINAL-LIQUID ADMINISTERING DEVICE

(71) Applicant: TERUMO KABUSHIKI KAISHA, Tokyo (JP)

(72) Inventor: Akira Kondo, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 240 days.

(21) Appl. No.: 15/678,329

(22) Filed: Aug. 16, 2017

(65) Prior Publication Data

US 2017/0368269 A1 Dec. 28, 2017

Related U.S. Application Data

(63) Continuation of application No. PCT/JP2016/053588, filed on Feb. 5, 2016.

(30) Foreign Application Priority Data

Feb. 20, 2015 (JP) ................................ 2015-031416

(51) Int. Cl.
*A61M 5/50* (2006.01)
*A61M 5/142* (2006.01)
(Continued)

(52) U.S. Cl.
CPC ........ *A61M 5/5086* (2013.01); *A61M 5/1452* (2013.01); *A61M 5/14248* (2013.01);
(Continued)

(58) Field of Classification Search
CPC .............. A61M 5/5086; A61M 5/1452; A61M 5/14248; A61M 2205/3327;
(Continued)

(56) References Cited

U.S. PATENT DOCUMENTS

2003/0233069 A1* 12/2003 Gillespie, Jr. ......... A61M 5/142
604/131
2010/0274180 A1* 10/2010 Donovan ........... A61B 17/8872
604/65

(Continued)

FOREIGN PATENT DOCUMENTS

CN 101563120 A 10/2009
CN 102083483 A 6/2011
(Continued)

OTHER PUBLICATIONS

International Search report issued in International Patent Application No. PCT/JP2016/053588 dated Apr. 19, 2016.
(Continued)

*Primary Examiner* — Lauren P Farrar
(74) *Attorney, Agent, or Firm* — Foley & Lardner LLP

(57) ABSTRACT

A medicinal-liquid administering device is for administering medicinal liquid filling a tubular body into a living body under a pressing action of a plunger. The medicinal-liquid administering device includes: a disposable part including: the tubular body, the plunger, and a movable part configured to be moved from an initial position and to press the plunger toward a distal-end side; a reusable part that is attachable to and detachable from the disposable part, the reusable part including: at least part of a driving part configured to move the movable part, a first position detection sensor configured to detect whether or not the movable part is at the initial position in a state before the movable part is moved, and an alarm part configured to output a first alarm when the first position detection sensor detects that the movable part is not at the initial position.

6 Claims, 4 Drawing Sheets

(51) Int. Cl.
*A61M 5/145* (2006.01)
*G01D 5/25* (2006.01)

(52) U.S. Cl.
CPC ..... *G01D 5/25* (2013.01); *A61M 2005/14506* (2013.01); *A61M 2205/18* (2013.01); *A61M 2205/33* (2013.01); *A61M 2205/3327* (2013.01); *A61M 2205/702* (2013.01); *A61M 2205/8206* (2013.01)

(58) Field of Classification Search
CPC ...... A61M 2205/18; A61M 2205/8206; A61M 2005/14506; A61M 2205/33; A61M 2205/702; G01D 5/25
See application file for complete search history.

(56) References Cited

U.S. PATENT DOCUMENTS

| | | | |
|---|---|---|---|
| 2015/0005703 A1 | 1/2015 | Hutchinson et al. | |
| 2015/0080790 A1* | 3/2015 | Munk | A61M 5/14566 604/67 |
| 2015/0297832 A1* | 10/2015 | Blomquist | F04B 51/00 73/168 |
| 2016/0074587 A1* | 3/2016 | Searle | G01F 11/027 604/189 |
| 2016/0287815 A1* | 10/2016 | Aoki | A61M 5/24 |

FOREIGN PATENT DOCUMENTS

| | | |
|---|---|---|
| EP | 1051986 A2 | 11/2000 |
| JP | 2004-532670 | 10/2004 |
| JP | 2007-511252 | 5/2007 |
| JP | 2009-525831 | 7/2009 |
| JP | 2010-501283 | 1/2010 |
| JP | 2010-526633 | 8/2010 |
| JP | 2013-503691 | 2/2013 |
| WO | WO-2004/030717 | 4/2004 |
| WO | WO-2014/089008 A3 | 7/2014 |
| WO | WO-2014/209591 A2 | 12/2014 |

OTHER PUBLICATIONS

European Search Report dated Jun. 19, 2018 in corresponding application No. 16752324.0.
Chinese Office Action dated Oct. 11, 2019 for corresponding Application No. 201680005124.6.

* cited by examiner

MEDICINAL-LIQUID ADMINISTERING DEVICE

CROSS REFERENCE TO RELATED APPLICATIONS

The present application is a bypass continuation of PCT Application No. PCT/JP2016/053588, filed on Feb. 5, 2016, which claims priority to Japanese Application No. 2015-031416, filed on Feb. 20, 2015. The contents of these application are hereby incorporated by reference in their entireties.

BACKGROUND

The present disclosure relates to a portable medicinal-liquid administering device that continuously or intermittently administers medicinal liquid filling a tubular body into a living body under a pressing action of a plunger.

Recently, a medicinal-liquid administering device that is configured so that the entire device is a disposable item is used. As a medicinal-liquid administering device of this type, for example, WO 2004/030717 A discloses a technical idea of outputting an alarm sound when a position detection sensor detects that a plunger has reached a predetermined position.

SUMMARY

However, when the entire device is configured as a disposable item, as in the conventional technique, there is a problem that running cost increases. As a method of solving such a problem, for example, it is conceivable to configure a medicinal-liquid administering device to be provided with a disposable part, which has a tubular body and a plunger and is disposable, and a reusable part.

In this medicinal-liquid administering device, a used disposable part should be prevented from being reused. Note that, even when the position detection sensor described in above described WO 2004/030717 A is used, whether the disposable part is unused or not cannot be detected because the position detection sensor is for detecting whether the plunger has reached the predetermined position. Thus, a used disposable part cannot be prevented from being reused.

The present disclosure has been developed in consideration of such a problem, and it is an object of certain embodiments of this disclosure to provide a medicinal-liquid administering device capable of reducing running cost and preventing a used disposable part from being reused.

A portable medicinal-liquid administering device according to one embodiment is for continuously or intermittently administering medicinal liquid filling a tubular body into a living body under a pressing action of a plunger. The medicinal-liquid administering device includes: a disposable part that is disposable and a reusable part that is provided to be attachable/detachable to/from the disposable part and is reusable; wherein the disposable part has the tubular body, the plunger, and a movable part that is moved from an initial position and presses the plunger toward a distal-end side; the reusable part has at least part of a driving part that moves the movable part; and the medicinal-liquid administering device further has a first position detection sensor that detects whether the movable part is at the initial position or not in a state before the movable part is moved, and an alarm part that outputs a first alarm when the first position detection sensor detects that the movable part is not at the initial position.

According to certain embodiments of the medicinal-liquid administering device, the disposable part, which is disposable, and the reusable part, which is reusable, are provided; therefore, running cost can be reduced. Moreover, whether the movable part is at the initial position or not is detected in the state before the movable part is moved, and the first alarm sound is output when it is not at the initial position; therefore, the used disposable part can be prevented from being reused.

In the above described medicinal-liquid administering device, the first position detection sensor may be provided in the reusable part. According to such a configuration, the constituent parts of the disposable part can be comparatively reduced. Therefore, the running cost can be further reduced.

In the above described medicinal-liquid administering device, the first position detection sensor may detect that the movable part is at the initial position by contacting the movable part. According to such a configuration, whether the movable part is at the initial position or not can be easily detected.

In the above described medicinal-liquid administering device, the first position detection sensor may detect whether the movable part is at the initial position or not when the reusable part is attached to the disposable part. According to such a configuration, the user can find out whether the disposable part is used or not when the reusable part is attached to the disposable part.

The above described medicinal-liquid administering device may have a second position detection sensor that detects whether or not the movable part moved from the initial position is at a predetermined position at which a remaining amount of the medicinal liquid in the tubular body becomes a predetermined amount; and, when the second position detection sensor detects that the movable part is at the predetermined position, the alarm part may output a second alarm. According to such a configuration, the user can be informed that the remaining amount of the medicinal liquid in the tubular body has become the predetermined amount.

In the above described medicinal-liquid administering device, the second position detection sensor may be provided in the reusable part. According to such a configuration, the constituent parts of the disposable part can be further reduced. Therefore, the running cost can be further reduced.

In the above described medicinal-liquid administering device, the driving part moves the movable part only toward the distal-end side of the plunger. According to such a configuration, the moved movable part does not return to the initial position. Therefore, whether the disposable part is unused or not can be reliably detected.

According to certain embodiments, because the disposable part, which is disposable, and the reusable part, which is reusable, are provided, the running cost can be reduced. Moreover, whether the movable part is at the initial position or not is detected in the state before the movable part is moved, and the first alarm sound is output when it is not at the initial position; therefore, the used disposable part can be prevented from being reused.

DETAILED DESCRIPTION

Hereinafter, a medicinal-liquid administering device according to embodiments of the present disclosure will be described with reference to attached drawings.

A medicinal-liquid administering device 10 according to the present embodiment is a portable-type medicinal-liquid administering device 10 that continuously or intermittently administers medicinal liquid, which fills a tubular body 18, into a living body under a pressing action of a plunger 20. In this case, the medicinal-liquid administering device 10 is a patch-type insulin pump. However, the medicinal-liquid administering device 10 is not limited to the patch type, but may be a tube type or the like.

Figure 1:
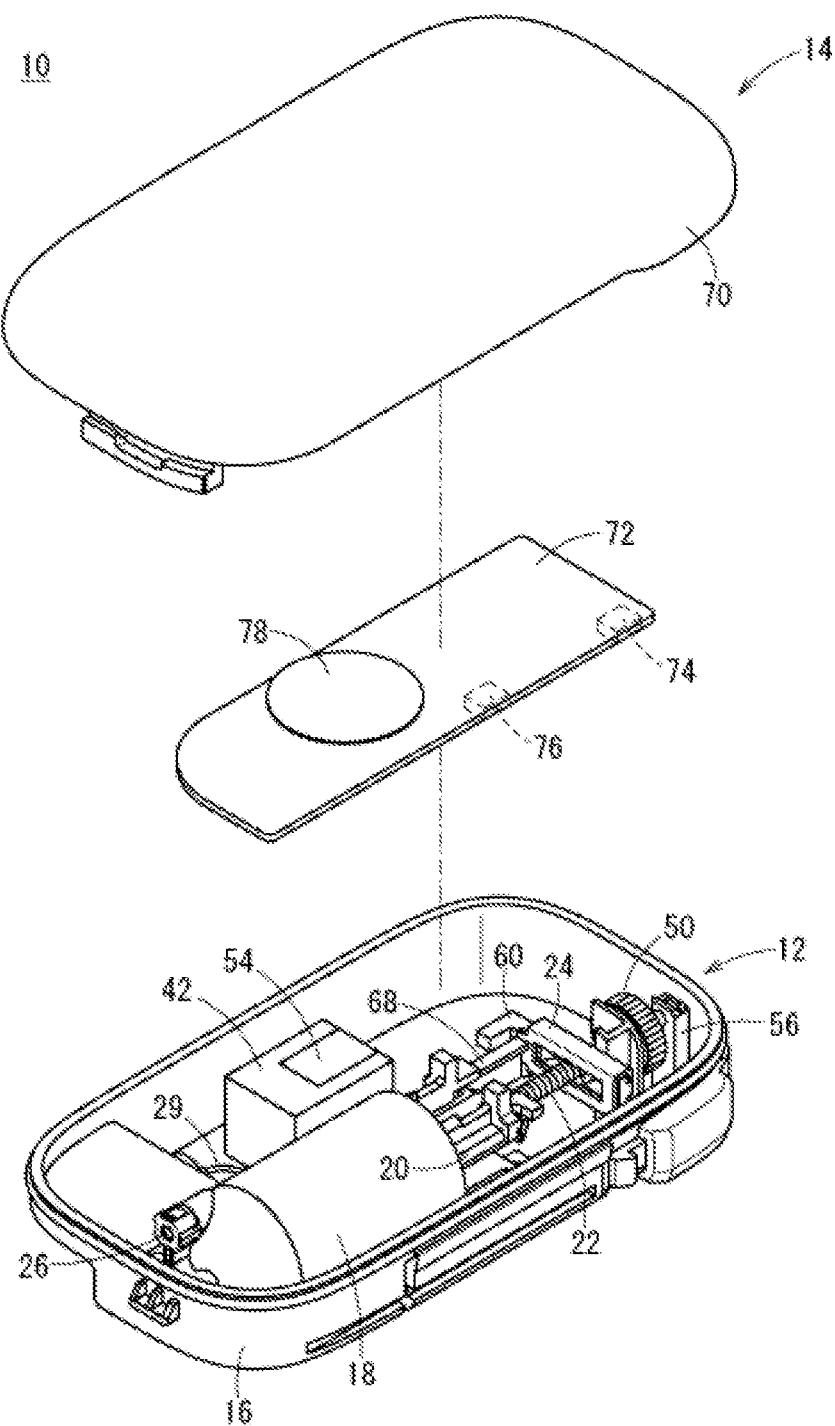
FIG. 1 is an exploded perspective view of a medicinal-liquid administering device according to one embodiment.

As shown in FIG. 1, the medicinal-liquid administering device 10 has a disposable part 12 and a reusable part 14, which is reusable. The disposable part 12 is provided with a base part 16 having a flat-box shape with one side opened, and the base part 16 forms an approximately rectangular shape in a planar view. The base part 16 is provided to be attachable/detachable to/from an unshown cradle, which can be pasted onto the skin of a user (patient). Note that the cradle includes a cannula, which is caused to indwell in the living body.

Figure 2:
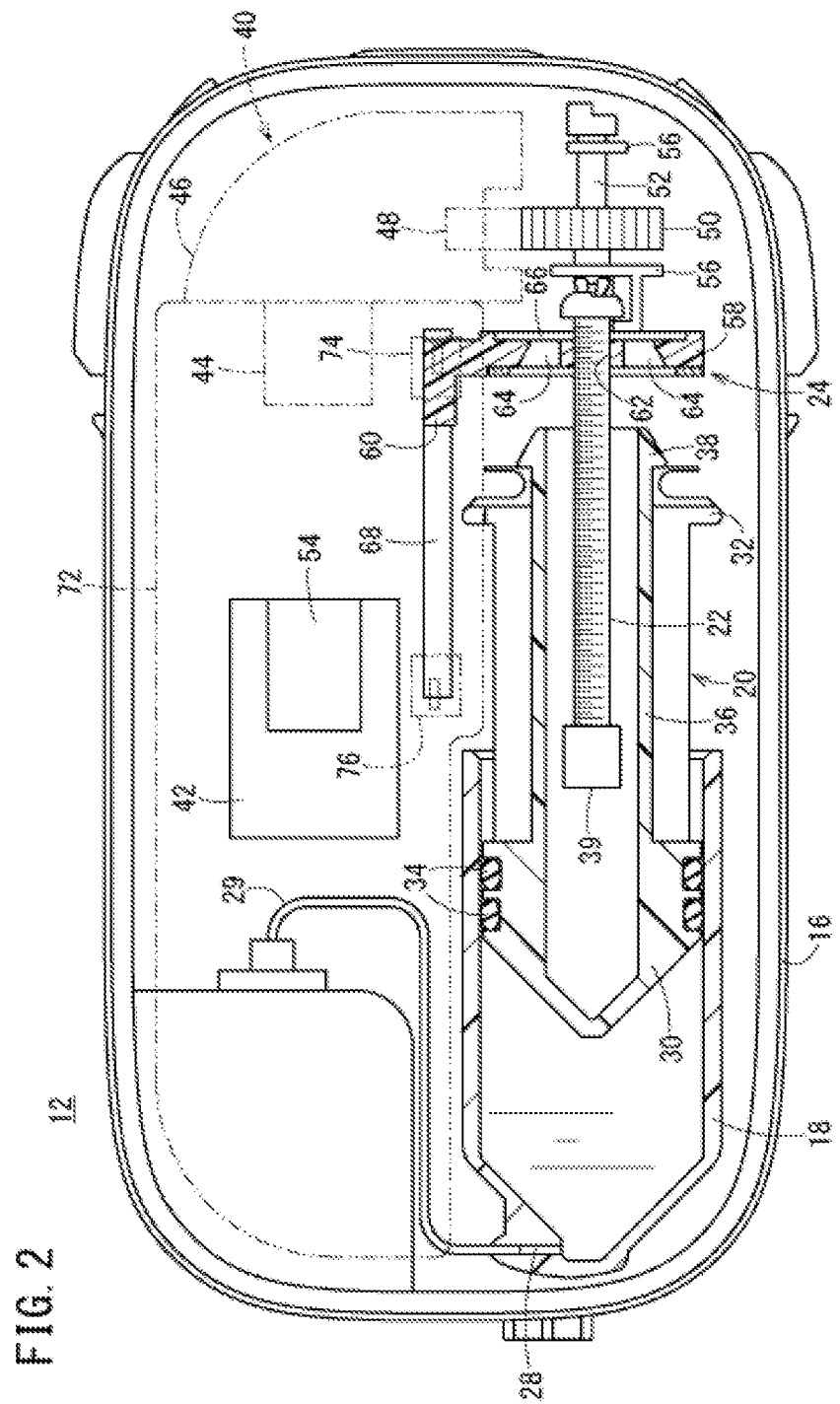
FIG. 2 is a partial cross-sectional explanatory view of a disposable part showing a state in which a nut part is at an initial position.

As shown in FIG. 2, the base part 16 is provided with the tubular body 18 filled with the medicinal liquid, the plunger 20 provided in the tubular body 18, a feed screw shaft 22 coaxially disposed with respect to the plunger 20, and a nut part (movable part) 24 screwed together with the feed screw shaft 22.

The tubular body 18 is extending in a cylindrical shape along a longitudinal direction of the base part 16. The outer diameter and the inner diameter of a distal-end part of the tubular body 18 are reduced toward a distal end. At the distal-end part of the tubular body 18 like this, a lead-in port 26 (see FIG. 1) for leading the medicinal liquid into the tubular body 18 and a lead-out port 28 for leading the medicinal liquid out from the inside of the tubular body 18 are formed. A lead-out tube 29, which leads the medicinal liquid in the tubular body 18 to the cannula, is communicated with the lead-out port 28.

The plunger 20 is integrally molded by using a resin material or the like and is provided in the tubular body 18 so as to be liquid-tightly slidable along the axial direction of the tubular body 18. The plunger 20 has a plunger main body 30, which constitutes a distal-end side, and a pusher 32, which is provided on the plunger main body 30 and constitutes a rear-end side. A pair of packings 34 are attached to the rear-end side of the plunger main body 30, which is formed in a cylindrical shape.

The pusher 32 is provided with a pair of extension parts 36, which are extending from the plunger main body 30 toward the rear to the outside of the tubular body 18, and a pair of claw parts 38, which are provided at rear-end parts of the extension parts 36. One end of the feed screw shaft 22 is pivotally supported by a bearing 39 and constitutes a driving part 40, which moves the nut part 24.

The driving part 40 further has: a battery 42 as a power source; a motor 44, which is driven by the battery 42; a gear box (power transmission mechanism) 46, which reduces and transmits the rotary driving force of the motor 44; and a transmission shaft 52, to which a spur gear 50 meshed with an output gear 48 of the gear box 46 is fixed and which is integrally rotatably locked to the feed screw shaft 22.

In the present embodiment, the battery 42 and the transmission shaft 52 are provided in the disposable part 12, and the motor 44 and the gear box 46 are provided in the reusable part 14. As a result of providing the motor 44 and the gear box 46 in the reusable part 14 in this manner, the cost of the disposable part 12 can be reduced.

The battery 42 is provided with a terminal 54, which is electrically connected to the motor 44 of the reusable part 14 when the reusable part 14 is attached to the disposable part 12. The transmission shaft 52 is pivotally supported by a pair of bearings 56, which are provided in the base part 16, in a state in which the transmission shaft 52 is disposed coaxially with the feed screw shaft 22.

The motor 44 is, for example, configured to be rotatable in a clockwise direction and be not rotatable in a counterclockwise direction. In other words, the motor 44 subjects the feed screw shaft 22 to rotary drive only in the direction in which the nut part 24 moves to the distal-end side of the plunger 20. However, the motor 44 may be configured to be rotatable in the clockwise direction and in the counterclockwise direction.

The nut part 24 is integrally molded by using a resin material and has a nut-part main body 58 formed in an approximately parallelepiped shape and a slide part 60 provided in the nut-part main body 58. In the nut-part main body 58, a screw hole 62, in which the feed screw shaft 22 is screwed, and a pair of through holes 64, which are formed so as to sandwich the screw hole 62 from both sides and are to insert the claw parts 38 therein, are formed. A reinforcing cover 66 formed of, for example, a metal material or the like is attached to the outer surface of the nut-part main body 58.

Figure 4:
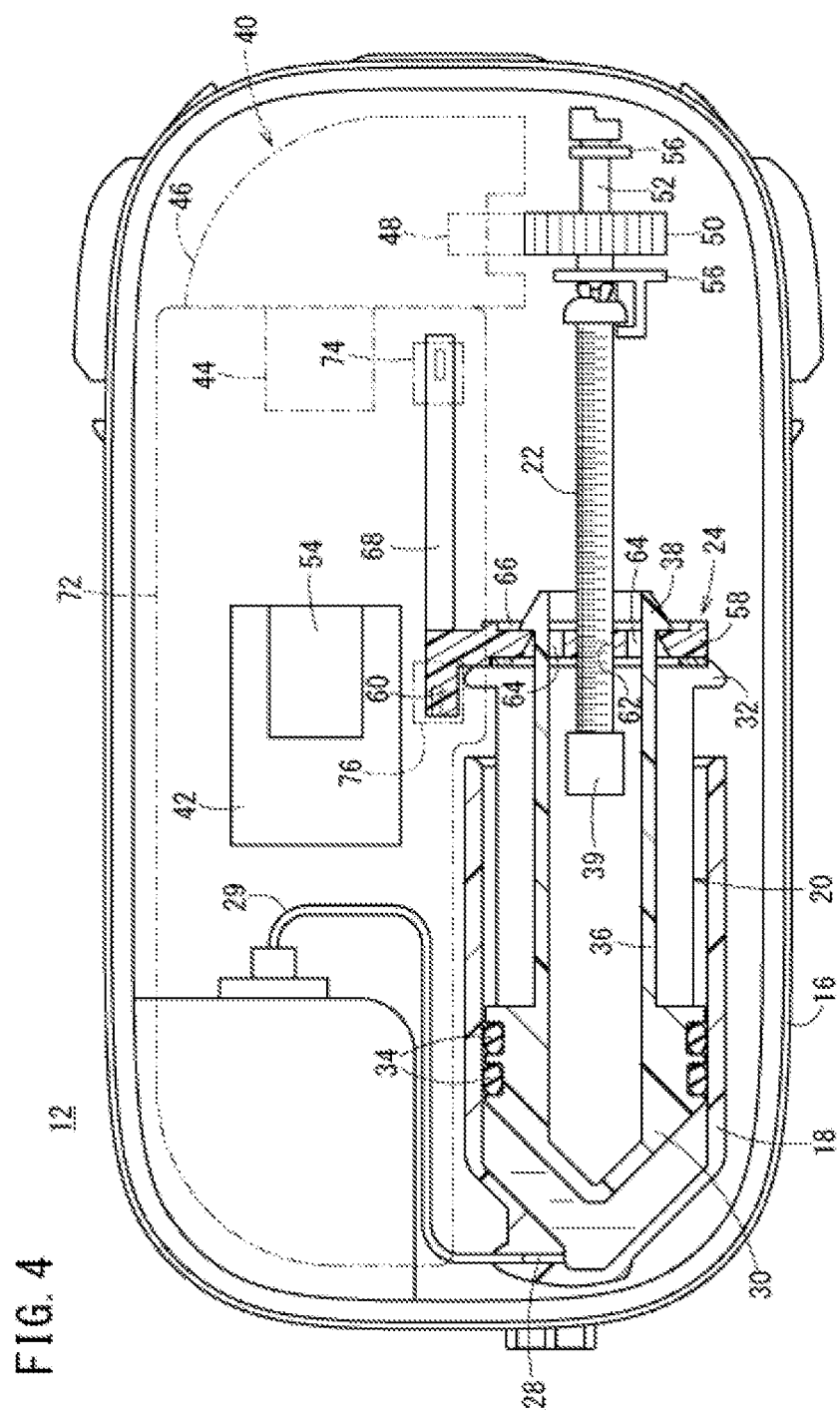
FIG. 4 is a partial cross-sectional explanatory view of the disposable part showing a state in which the nut part is at a predetermined position.

The slide part 60 slides with respect to a guide wall 68, which is provided in the base part 16 and is extending along the axial direction of the plunger 20. More specifically, in a state before usage, the nut part 24 is at an initial position at which it is not in contact with the plunger 20; and, under a rotary action of the feed screw shaft 22, the nut part 24 is moved from the initial position, contacts the plunger 20, and presses the plunger 20 to the distal-end side (see FIG. 4).

Figure 3:
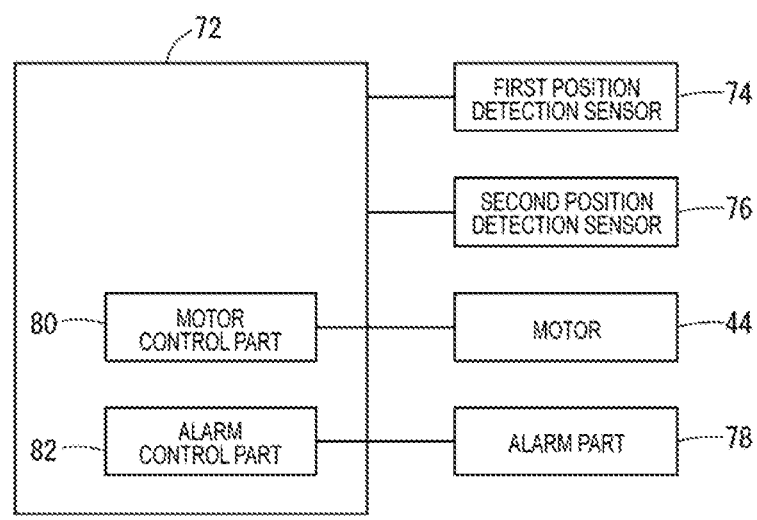
FIG. 3 is a control block diagram of the medicinal-liquid administering device of FIG. 1.

As shown in FIG. 1 to FIG. 3, the reusable part 14 is provided with a cover body 70, which is provided to be detachable from the base part 16 so as to close an opening of the base part 16, and a control part 72, which is provided on the cover body 70. A first position detection sensor (initial-position detection sensor) 74, a second position detection sensor (predetermined-position detection sensor) 76, the motor 44, and an alarm part 78 are electrically connected to the control part 72.

The first position detection sensor 74 is provided on the control part 72 and detects whether the nut part 24 is at the initial position or not in the state before movement of the nut part 24. Specifically, the first position detection sensor 74 is configured to be a contact sensor and is provided so as to contact the nut part 24 that is at the initial position in the state in which the reusable part 14 is attached to the disposable part 12. As a result of configuring the first position detection sensor 74 as the contact sensor in this manner, whether the nut part 24 is at the initial position or not can be easily detected.

The second position detection sensor 76 is provided on the control part 72 and detects whether the nut part 24 is at a predetermined position or not. Herein, the predetermined position refers to the position of the nut part 24 at the point when the remaining amount of the medicinal liquid in the tubular body 18 becomes a predetermined amount (for example, 0.5 cc). Specifically, the second position detection sensor 76 is configured to be a contact sensor and is provided so as to contact the nut part 24 at the predetermined position in the state in which the reusable part 14 is attached to the disposable part 12. As a result of configuring the second position detection sensor 76 as the contact sensor like this, whether the nut part 24 is at the predetermined position or not can be easily detected. However, the first position detection sensor 74 and the second position detection sensor 76 may be non-contact sensors instead of contact sensors.

The alarm part 78 is configured to be able to output, for example, first to third alarm sounds. At least one of the frequency, amplitude, output time, and the number of times of outputs of each of the first to third alarm sounds is different so that the user can easily distinguish the first to third alarm sounds. However, the first to third alarm sounds may be set to have mutually the same frequencies, amplitudes, output time, and the numbers of times of outputs.

The control part 72 is provided with a motor control part 80 and an alarm control part 82. The motor control part 80 subjects the motor 44 to drive control based on the information about medicinal-liquid administration transmitted from a remote controller.

When the first position detection sensor 74 detects that the nut part 24 is not at the initial position, the alarm control part 82 outputs the first alarm sound from the alarm part 78. Meanwhile, when the second position detection sensor 76 detects that the nut part 24 is at the predetermined position, the alarm control part 82 outputs the second alarm sound from the alarm part 78. Furthermore, when the number of rotations of the motor 44 reaches a predetermined number of rotations after the presence of the nut part 24 at the predetermined position is detected by the second position detection sensor 76, the alarm control part 82 outputs the third alarm sound from the alarm part 78.

The medicinal-liquid administering device 10 according to the present embodiment is basically configured in the above described manner, and operations and working effects thereof will next be described. First, the user takes out the disposable part 12 from a packaging container. In this state, the tubular body 18 of the disposable part 12 is not filled with the medicinal liquid, and the nut part 24 is at the initial position at which it is not in contact with the plunger 20 (see FIG. 2).

Then, the user adjusts the position of the plunger 20 with respect to the tubular body 18 and fills the tubular body 18 with an appropriate amount of medicinal liquid from a medicinal liquid container such as a vial in which the medicinal liquid is stored in a hermetically sealed manner. Then, the reusable part 14 is attached to the disposable part 12. As a result, the electric power of the battery 42 of the disposable part 12 is supplied to the constituent parts of the reusable part 14, and the output gear 48 of the gear box 46 of the reusable part 14 is meshed with the spur gear 50 of the disposable part 12. The control part 72 is activated in response to the supply of the electric power of the battery 42, and the first position detection sensor 74 starts detecting whether the nut part 24 is at the initial position or not in the state before movement of the nut part 24.

When the first position detection sensor 74 detects that the nut part 24 is not at the initial position in the state before the nut part 24 is moved (when the first position detection sensor 74 is in an off state), the alarm control part 82 causes the alarm part 78 to output the first alarm sound. By virtue of this, the user can find out that the disposable part 12 is used; therefore, a measure such as replacing the used disposable part 12 with an unused item can be taken. Thus, the user can be prevented from erroneously reusing the used disposable part 12.

On the other hand, when the first position detection sensor 74 detects that the nut part 24 is at the initial position in the state before the nut part 24 is moved (when the first position detection sensor 74 is in an on state), the alarm control part 82 does not output the alarm sound from the alarm part 78 because the disposable part 12 is unused.

Subsequently, the user carries out priming of the medicinal-liquid administering device 10. Specifically, the remote controller is operated to subject the motor 44 to rotary drive. As a result, the rotary driving force of the motor 44 is transmitted to the feed screw shaft 22 via the gear box 46, the spur gear 50, and the transmission shaft 52. Therefore, the feed screw shaft 22 is rotated, and the nut part 24 advances toward the plunger 20 while sliding on the guide wall 68.

When the nut part 24 advances to the distal-end side of the plunger 20, the pair of claw parts 38 abut the wall surfaces constituting the through holes 64 of the nut part 24, and the pair of extension parts 36 are warped so as to get close to each other. Then, when the claw parts 38 go through the through holes 64, the claw parts 38 return to the original positions, thereby locking the nut part 24 with respect to the plunger 20. As a result, the nut part 24 can press the plunger 20 toward the distal-end side. Then, when the nut part 24 is caused to further advance, the medicinal liquid in the tubular body 18 is pressed by the plunger 20, the inner hole of the lead-out tube 29 is filled with the medicinal liquid, and the priming is completed.

Subsequently, the user pastes the unshown cradle at a predetermined position of the skin and causes the cannula locked with the cradle to indwell in the living body by using a needling mechanism. Then, when the disposable part 12 and the reusable part 14 are attached to the cradle, the lead-out tube 29 and the cannula are communicated with each other; and, when the motor control part 80 subjects the motor 44 to rotary control, the medicinal liquid in the tubular body 18 is continuously or intermittently administered into the living body.

At this point, the second position detection sensor 76 detects whether the nut part 24, which has been moved from the initial position, is at the predetermined position or not. When the second position detection sensor 76 detects that the nut part 24 is not at the predetermined position (when the second position detection sensor 76 is in an off state), the alarm control part 82 does not output the alarm sound by the alarm part 78.

On the other hand, when the second position detection sensor 76 detects that the nut part 24, which has been moved from the initial position, is at the predetermined position (when the second position detection sensor 76 is in an on state), the alarm control part 82 causes the alarm part 78 to output the second alarm sound. By virtue of this, the user can find out that the remaining amount of the medicinal liquid in the tubular body 18 is the predetermined amount. Therefore, for example, when the medicinal liquid in an amount larger than the predetermined amount is to be intermittently administered, a measure such as replacing the disposable part 12 with an unused item can be taken.

Then, when the number of rotations of the motor 44 after the second position detection sensor 76 has become the on state reaches a predetermined number of rotations, the alarm control part 82 causes the alarm part 78 to output the third alarm sound. By virtue of this, the user can find out that the remaining amount of the medicinal liquid in the tubular body 18 has become empty.

According to the present embodiment, the medicinal-liquid administering device 10 is provided with the disposable part 12, which is disposable, and the reusable part 14, which is reusable; therefore, running cost can be reduced. Moreover, whether the nut part 24 is at the initial position or not is detected in the state before the nut part 24 is moved, and the first alarm sound is output from the alarm part 78 when it is not at the initial position; therefore, the used disposable part 12 can be prevented from being reused.

In the present embodiment, because the first position detection sensor 74 and the second position detection sensor 76 are provided on the control part 72 of the reusable part 14, the constituent parts of the disposable part 12 can be comparatively reduced. By virtue of this, running cost can be further reduced.

Moreover, because the driving part 40 (motor 44) moves the nut part 24 only to the distal-end side of the plunger 20, the moved nut part 24 does not return to the initial position. Therefore, whether the disposable part 12 is unused or not can be reliably detected.

In the present embodiment, the alarm part 78 is not limited to the examples of outputting the first to third alarm sounds, but may inform the user by outputting sounds, lighting or blinking a display light (s), displaying characters by a display, vibrations, or the like. Meanwhile, the alarm part 78 like this may be provided on the remote controller.

In the present embodiment, at least one of the first position detection sensor 74 and the second position detection sensor 76 may be provided in the disposable part 12.

What is claimed is:

1. A medicinal-liquid administering device for continuously or intermittently administering medicinal liquid filling a tubular body into a living body under a pressing action of a plunger, the medicinal-liquid administering device comprising:
    a disposable part comprising:
        the tubular body,
        the plunger,
        a power source, and
        a movable part configured to be moved from an initial position, to be locked with the plunger, and to press the plunger in a distal direction;
    a reusable part that is attachable to and detachable from the disposable part, the reusable part comprising at least part of a driving part configured to move the movable part only in the distal direction;
    a first position detection sensor configured to, in response to a supply of electric power from the power source when the reusable part is attached to the disposable part, detect whether or not the movable part is at the initial position in a state before the movable part is moved; and
    an alarm part configured to output a first alarm when the first position detection sensor detects that the movable part is not at the initial position in the state before the movable part is moved,
    wherein the movable part is not locked with the plunger in the state before the movable part is moved.

2. The medicinal-liquid administering device according to claim 1, wherein:
    the first position detection sensor is located in the reusable part.

3. The medicinal-liquid administering device according to claim 1, wherein:
    the first position detection sensor is configured to detect that the movable part is at the initial position by contacting the movable part.

4. The medicinal-liquid administering device according to claim 1, further comprising:
    a second position detection sensor configured to detect whether or not the movable part is at a predetermined position at which a remaining amount of the medicinal liquid in the tubular body is at a predetermined amount,
    wherein, when the second position detection sensor detects that the movable part is at the predetermined position, the alarm part outputs a second alarm.

5. The medicinal-liquid administering device according to claim 4, wherein:
    the second position detection sensor is located in the reusable part.

6. A control method of a portable medicinal-liquid administering device for continuously or intermittently administering medicinal liquid filling a tubular body into a living body under a pressing action of a plunger, the method comprising:
    providing a medicinal-liquid administering device comprising:
        a disposable part comprising:
            the tubular body,
            the plunger,
            a power source, and
            a movable part configured to be moved from an initial position, to be locked with the plunger, and to press the plunger in a distal direction, and
        a reusable part that is attachable to and detachable from the disposable part, the reusable part comprising at least part of a driving part configured to move the movable part only in the distal direction;
    in response to a supply of electric power from the power source when the reusable part is attached to the disposable part, detecting whether or not the movable part is at the initial position in a state before the movable part is moved; and
    outputting a first alarm when the movable part is detected to be not at the initial position in the state before the movable part is moved,
    wherein the movable part is not locked with the plunger in the state before the movable part is moved.

* * * * *